United States Patent [19]

Meyer

[11] Patent Number: 4,990,740
[45] Date of Patent: Feb. 5, 1991

[54] INTRA-MICROSPRAY ICP TORCH

[75] Inventor: Gerhard A. Meyer, Midland, Mich.

[73] Assignee: The Dow Chemical Company, Midland, Mich.

[21] Appl. No.: 320,002

[22] Filed: Mar. 6, 1989

[51] Int. Cl.[5] .......... B23K 9/00

[52] U.S. Cl. .......... 219/121.52; 219/121.51; 219/121.49; 219/121.48; 315/111.51; 239/343; 239/432

[58] Field of Search .......... 219/121.5, 121.52, 121.48, 219/121.51, 121.49; 239/338, 343, 370, 432; 261/78.2, DIG. 65; 315/111.51, 111.21

[56] References Cited

U.S. PATENT DOCUMENTS

| | | | |
|---|---|---|---|
| 727,415 | 5/1903 | McDermott | 219/121 PY |
| 3,923,288 | 12/1975 | King | 239/432 |
| 4,084,934 | 4/1978 | Kumazawa | 239/432 |
| 4,177,945 | 12/1979 | Schwartz et al. | 261/78.2 |
| 4,206,160 | 6/1980 | Suddendorf et al. | 261/78 A |
| 4,251,033 | 2/1981 | Rich et al. | 239/370 |
| 4,482,246 | 11/1984 | Meyer et al. | 356/316 |
| 4,551,609 | 11/1985 | Falk | 315/111.51 |
| 4,575,609 | 3/1986 | Fassel et al. | 219/121 PY |
| 4,739,147 | 4/1988 | Meyer et al. | 219/121 PM |
| 4,746,067 | 5/1988 | Svoboda | 239/370 |

FOREIGN PATENT DOCUMENTS

| | | |
|---|---|---|
| 2103362 | 8/1972 | Fed. Rep. of Germany . |
| 3422946 | 1/1986 | German Democratic Rep. . |

OTHER PUBLICATIONS

"Direct Liquid Sample Introduction for Flow Injection Analysis and Liquid Chromatography with Inductively Coupled Argon Plasma Spectrometric Detection" by Kimberly Lawrence, Gary W. Rice, and Velmer A. Fassel, Analytical Chemistry, 1984.

*Primary Examiner*—M. H. Paschall
*Attorney, Agent, or Firm*—Wood, Herron & Evans; Timothy S. Stevens

[57] ABSTRACT

An intra-microspray ICP torch for use in conjunction with spectographic analysis generates a high temperature ionized gas in a plasma region at one end of the torch, and includes a preshaped tube mounted within the torch, with a first end of the tube terminating adjacent the plasma region, and a nebulizer mounted to a second end of the tube. The preshaped tube has at least one set of impactors that define at least two chambers, the impactors blocking the line of sight between adjacent chambers. The nebulizer propels a pressurized aerosol/sample mixture at the impactors, toward the plasma region. The impactors divert the mixture as it travels from chamber to chamber toward the plasma region, causing a filtering effect that promotes passage to the plasma region of sample particles having a size of about 15 microns or less, thereby resulting in optimum spectrographic clarity.

22 Claims, 3 Drawing Sheets

INTRA-MICROSPRAY ICP TORCH

FIELD OF THE INVENTION

This invention relates to an inductively coupled plasma torch that is used in conjunction with a spectrometer for the purpose of elemental analysis.

BACKGROUND OF THE INVENTION

In an inductively coupled plasma torch, referred to as an ICP torch, a gas is ionized in a plasma region located at one end of the torch and a sample is injected or introduced into the plasma region, the sample becoming atomized to enable elemental detection by a number of techniques, including spectrometric analysis. A prealigned demountable plasma torch is disclosed in applicant'U.S. Pat. No. 4,739,147, expressly incorporated herein by reference in its entirety.

To obtain optimal analytical performance with an ICP torch, particularly for interfacing spectrographic analysis with chromatography, it is desirable to introduce the sample into the plasma region in the form of a finely dispersed particle mist at a relatively constant flow. It is commonly accepted within the industry that the size of the sample particles reaching the plasma region should be less than about 15 microns. In order to prevent the introduction to the plasma region of larger sized particles, prior devices have utilized a nebulizer in conjunction with some type of large volume particle size discrimination chamber.

For systems of this type, a liquid sample to be analyzed and an aerosol gas are fed into a nebulizer mounted within the large volume chamber, which, for example, by means of double pass baffling systems, produces an aerosol mixture of sample and gas. The chamber is connected by a suitable joint for fluid communication with a first end of an internal sample pass tube of an ICP torch. The tube extends through the ICP torch and has a second end terminating adjacent the plasma region, wherein subsequent atomization of the sample occurs.

To reach the plasma region, and eventual atomization, the sample must pass from the nebulizer, through the large volume container and through the internal tube. At typical operating pressures and gas flow rates, only the smaller sized particles remain suspended long enough to traverse this route. The relatively large droplets, i.e., those greater than 15 microns, that exit the nebulizer contact and condense upon the walls of the spray chamber, for collection through an outlet as waste. A large volume discrimination chamber of this type has a volume of about 125 milliliters (cubic centimeters). The liquid sample can be pumped to the nebulizer by a peristaltic pump at a rate of between 0.1 and 1 milliliter per minute, while the aerosol gas is input to the nebulizer at a pressure ranging from about 15-30 psi, resulting in a flow rate of gas into the nebulizer of about one liter per minute.

Systems of this type generally provide a relatively slow, steady flow of sample into the plasma region, which results in increased residence time of the sample while in the plasma region. Increased residence time produces more thorough atomization of the sample particles, and thus is desirable for clarity in analysis. However, due to the relatively slow sample flow rate, which for these systems is directly dependent upon the nebulizer pressure setting, only about 1 to 3% of the liquid sample introduced into the nebulizer actually reaches the plasma region. In other words, there is a trade off between clarity and efficiency, and the nebulizer pressure setting must be chosen so as to affect a compromise between these two concerns. An increase in pressure will result in an increase in the percentage of sample that is introduced to the plasma region, but a decrease in the effective atomization of the particles that are introduced.

This concern becomes particularly acute when organic samples are to be tested. Organic sample particles tend to be heavier then corresponding inorganic sample particles, and thus require a higher operating pressure in order to overcome the effects of gravity and remain suspended long enough to reach the plasma region. However, increased pressure may produce excessive formation of vapor together with the sample particles, which can adversely affect the clarity of spectral lines during testing.

In addition to low efficiency, the relatively large "dead volume" of the spray chamber makes it more difficult to maintain clarity during high resolution chromatography, in which the intensity of the discharge is measured in the time domain. Typically, in liquid chromatography, a pure liquid sample of several compounds undergoes a size exclusion step prior to being introduced to the nebulizer of the ICP torch. This size exclusion step separates the compounds according to molecular size. Thus, the different compounds successively pass through the torch for ionization in the plasma region, according to molecular size, whereupon they are analyzed during the time period in which they are in the plasma region. In high resolution chromatography, it is important to distinguish the different compounds, or to detect the transition between successive compounds. However, because the large "dead volume" occupied by the input sample tends to slow sample flow, it becomes difficult to visually discern the transition between a first atomized compound and the compound atomized immediately thereafter.

The relatively large volume chamber also results in lost time during testing. When changeover to another sample is required, the relatively large volume spray chamber must be thoroughly cleaned in order to assure the accuracy of any subsequent testing. Then, before testing starts up again, the entire discrimination chamber volume must be filled before any of the sample reaches the plasma region. Ultimately, for a large number of tests the cumulative time required to clean and to refill the large volume spray chamber represents a substantial loss in testing time.

Others have attempted to overcome the disadvantages associated with large volume chamber systems of this type. For example, Fassel et al. U.S. Pat. No. 4,575,609 is directed to a direct injection nebulizer that is designed to overcome dead volume problems associated with prior systems. This is partially accomplished by maintaining an aerosol flow through the nebulizer orifice into the plasma region at a velocity not less than 100 meters per second. According to this patent, a micro nebulizer that extends through the torch has inner and outer concentric tubes that terminate just short of the plasma region. Liquid solvent and a source of sample liquid are pumped through the inner tube, while nebulizing gas is pumped through the outer tube. With this structure, nebulization occurs adjacent to, or within, the plasma region and just prior to atomization. Nearly 100% of the sample enters the plasma region.

Compared to the prior large volume systems, the smaller volume, less than about 5 microliters, and preferably about 2.5 microliters, and the increased velocity at the orifice, about b 100 m/s, reduce problems associated with dead volume.

There are practical disadvantages associated with direct injection nebulizers of this type. In order to maintain an aerosol flow rate of about 100 meters per second, the pump must be operated at a relatively high pressure ranging from about 100 to 1000 psi. A typical peristaltic pump used for the prior large volume systems is not capable of operating under such high nebulizer back pressures, and thus, new equipment must be purchased in order to operate the direct injection nebulizer. Additionally, operation costs are increased due to the increased energy expended in operating a pump at these relatively high pressures. The micro nebulizer is also extremely susceptible to breakage, due to the fact that the outer tube is tapered to within a distance of less than 0.05 mm from the inner tube.

The direct injection nebulizer also suffers in analytical performance characteristics. Due to the high flow rate, the residence time of sample particles in the plasma region is reduced. The relatively high flow rate, the small volume tube and the micro nebulizer orifice also combine to produce excessive sample turbulence, sometimes referred to as flicker, within the plasma region. This flicker affects the magnitude of the emission signal that is sensed by the spectrometer. Additionally, because the micro nebulizer orifice is located directly adjacent to the plasma region, the direct injection nebulizer does not discriminate sample particles by size. There is no assurance whatsoever that sample particles being introduced into the plasma region have a size of less than 15 microns. In fact, most particles are not within the desired size range.

In other words, while a direct injection nebulizer of this type may reduce some of the efficiency problems associated with large volume discrimination chamber systems, it also introduces a number of other problems, both practical and analytical.

It is an object of this invention to provide an ICP torch that promotes the efficient introduction of small sized sample particles into a plasma region at a constant flow rate, while at the same time overcoming disadvantages associated with prior large volume discrimination chamber systems and with direct injection nebulizer systems.

SUMMARY OF THE INVENTION

This invention contemplates the use of multiple chambers, located within the ICP torch, for filtering sample particles according to size as they move toward the plasma region.

This invention also contemplates the use of flow diverting impactors to provide particle discrimination according to size as the sample particles move from the nebulizer toward the plasma region. The impactors produce a filtering effect that permits only those sample particles having a size of about 15 microns or less to reach the plasma region, thereby optimizing clarity in spectrographic analysis.

To these ends, in accordance with a preferred embodiment of the invention, an ICP torch includes: means for generating a high temperature ionized gas in a plasma region at one end of the torch; multichamber particle discrimination mounted concentrically within the torch with a first end terminating adjacent the plasma region; and, a nebulizer mounted to a second end of the multichamber particle discrimination means to direct a pressurized aerosol/sample mixture therethrough toward the plasma region. The multichamber particle communication means includes an inner, preshaped tube having multiple chambers, and flow diverting impactors, or impaction means, which define the multiple chambers. The impactors completely block the line of sight between adjacent chambers, causing pressurized sample that is propelled therethrough by the nebulizer to be diverted from a linear path while enroute to the plasma region. Only the smaller, lighter particles will be swept around the impactors, and toward the plasma region. The larger particles will either condense or break into smaller particles upon contacting the impactors or the walls of the tube. Thus, in operation, the multichamber particle discrimination means produces a filtering effect, whereby the sample particles are broken down, or discriminated, according to size. As a result, the sample is introduced into the plasma region at a steady flow rate and in the form of a finally dispersed particle mist, thereby assuring optimum spectrographic clarity.

Preferably, two spaced sets of impaction fingers are provided, defining three chambers of the preshaped tube. The nebulizer is mounted to be in direct communication with a first of the chambers, the bottommost chamber, and is aimed directly at a first, or lower, set of impaction fingers which separate the first chamber from a second chamber residing thereabove. The third chamber is located above the second chamber, separated therefrom by an upper, or second, set of impaction fingers. The third chamber has an outlet nozzle located adjacent to the plasma region. Each set of impaction fingers preferably includes three fingers that are directed radially inward to substantially block the line of sight path between adjacent chambers. So as not to completely block the fluid path between adjacent chambers, it may be required to stagger, or offset, the fingers somewhat along the length of the tube.

When a pressurized sample mixture is introduced by the nebulizer into the first chamber, toward the first set of impaction fingers, the heavier, wetter particles will either contact and condense upon the fingers or the interior surface of the first chamber, or break into smaller particles. Further disintegration of the larger secondary particles by collision into, or with, the high speed primary particles may also occur. The smaller, lighter particles will be swept or diverted around the fingers and into the second chamber. As the particles continue upward toward the second set of impaction fingers, the relatively heavy particles will fall downward under the force of gravity, or contact and condense upon the interior walls of the tube or the fingers, or again, break into smaller particles. Sample particles that condense upon contact with the walls will eventually flow downward under the force of gravity into the first chamber, for collection via a waste duct. Those particles that remain suspended continue travelling upward and into the third chamber. Eventually, only the smaller, drier particles, i.e., those less than 15 microns, exit the nozzle of the third chamber and reach the plasma region.

It has been noted during experimentation that, while one set of impactor fingers may provide sufficient particle discrimination for some samples, the sample flow into the plasma region is significantly less turbulent when two spaced sets of fingers are used. The second set of fingers serves as a dampening mechanism to attenuate this turbulence. Therefore, in the interest of spectral clarity, it is preferable that the preshaped tube includes two spaced sets of impaction fingers. Two sets of fingers are considered optimal, as additional sets will cause excessive surface area contact and result in the sample flow being too slow.

Compared to prior art systems that utilize a conventional large volume spray chamber, the reduced sized multichamber particle discrimination means of this invention, i.e., about 2.5 millimeters, overcomes resolution problems associated with dead volume, reduces the time required for cleaning, reduces the elapsed throughput time during changeover to a new sample, and produces an increase in the percentage of sample particles that reach the plasma region.

Compared to the direct injection nebulizers described previously, the ICP torch of this invention is less susceptible to breakage, and it can be operated at a much lower pressure, allowing the use of a conventional peristaltic pump. Use of a conventional peristaltic pump represents both a savings in energy and cost in retrofitting prior systems. With regard to clarity: this invention constitutes an improvement over the direct injection nebulizer because only particles sized less than 15 microns reach the plasma region; the two spaced sets of impaction fingers promote a steady flow of sample into the plasma region; and the multiple chambers and impactors increase sample residence time in the plasma region by slowing the sample flow to a speed more advantageous for spectrochemical analysis.

These and other features of the invention will be more readily appreciated in view of the detailed description and the drawings in which:

DETAILED DESCRIPTION OF THE INVENTION

Figure 1:
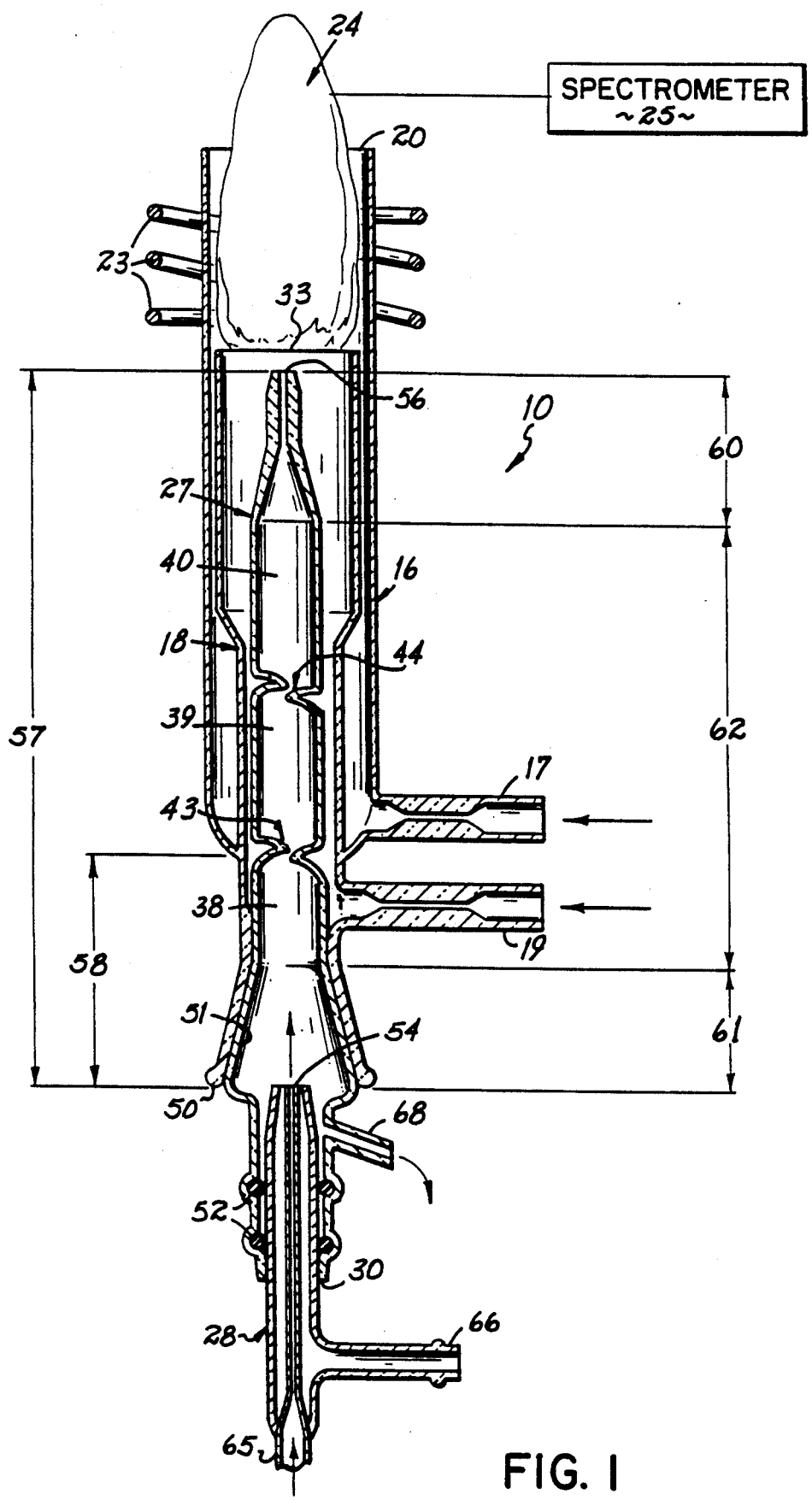
FIG. 1 is a cross-sectional schematic depicting an ICP torch in accordance with a preferred embodiment of the invention.

FIG. 1 shows an intra-microspray ICP torch 10 in accordance with a preferred embodiment of the invention. The torch 10 includes an exterior tube 16 into which coolant gas is introduced through an input duct 17. The coolant gas may be argon or any other inert gas. Preferably, the coolant duct 17 is connected tangentially to exterior tube 16 so that the coolant gas flows in a helical pattern about an intermediate tube 18 mounted concentric within exterior tube 16. Plasma gas is introduced to intermediate tube 18 through a gas input duct 19. Again, this plasma gas is preferably argon, but may be any inert gas that is easily ionized. Input duct 19 is also preferably tangentially connected so as to provide a helical flow path for the plasma gas entering the intermediate tube 18.

At a first end 20 of the torch 10, a surrounding coil 23 provides a radio frequency energy source for inductively heating the plasma 24 to make it electrically conductive as gases are introduced through tubes 16 and 18. The light produced by the high temperature ionized gas in the plasma region 24 may be analyzed by a spectrometer 25 or similar wavelength selective measuring device. Light emitted from the plasma region 24 is resolved by the spectrometer into distinguishable lines. The positions of these lines within a spectrum indicate the chemical composition of the ionized gas. For accurate analysis, it is absolutely critical that the sample be introduced into the plasma region 24 at a steady rate, and in relatively small sized particles having a size of less than 15 microns. Otherwise, if larger size particles or wet condensate particles enter the plasma region 24, the resulting spectral lines will lack clarity and the accuracy of spectrometric analysis will suffer.

In accordance with a preferred embodiment of the invention, means for introducing a sample into the plasma region 24 includes multichamber particle discrimination means, or a preshaped tube 27, located in the torch 10. A nebulizer 28 is removably mounted within a bottom end 30 of the tube 27. A type C concentric nebulizer made to the desired specifications by the Precision Glassblowing Co. of Colorado has proved suitable. The preshaped tube 27 extends upwardly through the intermediate tube 18 substantially the length thereof, terminating just short of an upper end 33 of the intermediate tube 18 and adjacent to the plasma region 24. The preshaped tube 27 conveys the sample from the nebulizer 30 to the plasma region 24. While enroute, the preshaped tube 27 discriminates the sample particles according to size, preventing the larger particles from reaching the plasma region and promoting a steady flow into the plasma region 24 of sample particles that have a size of less than about 15 microns.

To achieve sufficient particle discrimination, the multichamber particle discrimination means 27 is divided into at least two chambers, the chambers being separated by impactors, or impaction means. The impactors extend radially inward to block the line of sight path between the chambers, thereby diverting linear sample flow between adjacent chambers while enroute to the plasma region 24. Instead, the sample must flow around the impactors. The utilization of multiple chambers and impactors that are actually located within the torch, i.e., concentrically within tube 18 and proximate to the plasma region 24, represents an efficient use of space and, at the same time, results in optimum clarity for spectrographic analysis.

Preferably, the tube 27 has three chambers that are defined by two spaced sets of impaction fingers. The nebulizer 28 is mounted to preshaped tube 27 so as to communicate with a first or bottommost chamber 38. A second or middle chamber 39 is located above first chamber 38, and a third, or upper chamber 40 is located above second chamber 39. A lower set 43 of impaction fingers is located between the first and second chambers, while an upper set 44 of impaction fingers is located between the second and third chambers. Each set of impaction fingers blocks the direct, linear path between the chamber located below and the chamber located above. The nebulizer 28 is mounted to the tube 27 so as to be aimed directly at the lower set 43 of impactors.

Figure 2:
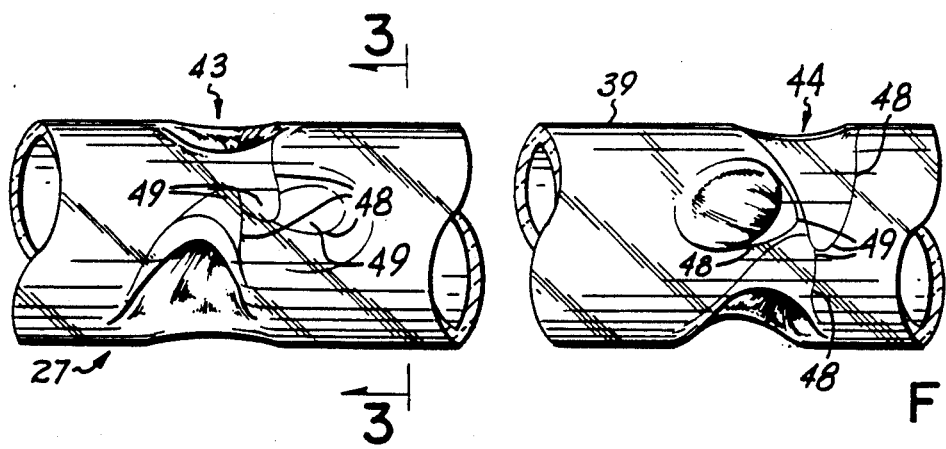
FIG. 2 is an enlarged, plan view of the preshaped tube that extends through the ICP torch in accordance with a preferred embodiment of the invention.
Figure 3:
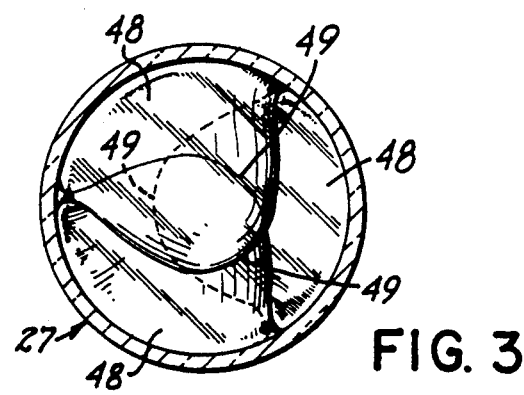
FIG. 3 is a cross-sectional view taken along lines 3—3 of FIG. 2.
Figure 4:
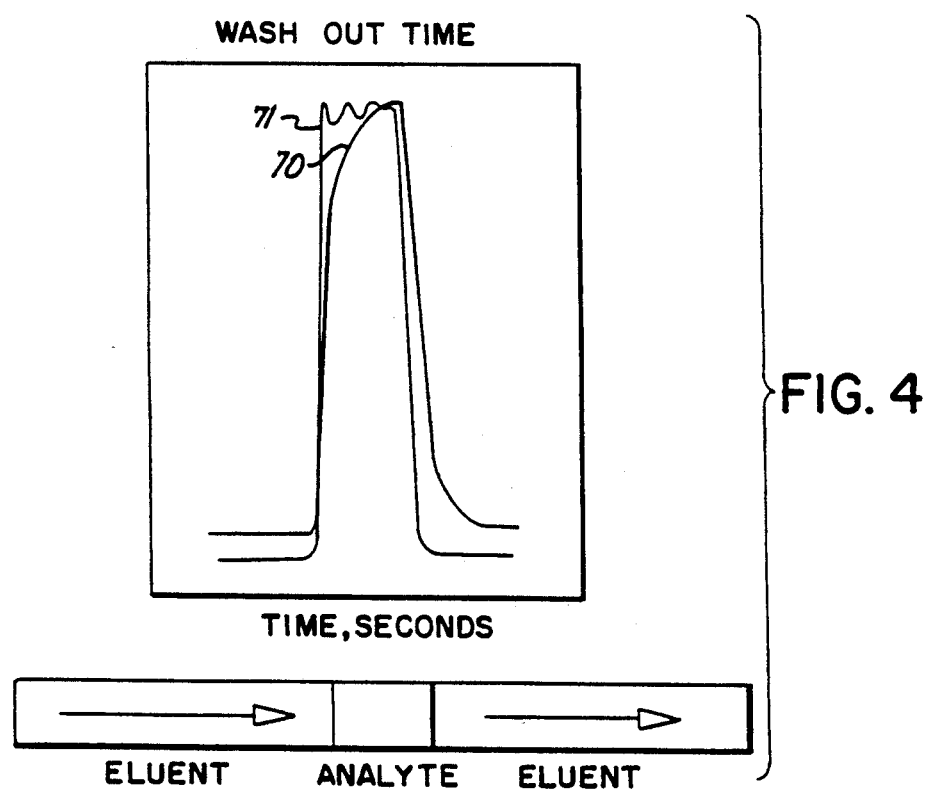
FIG. 4 illustrates a comparison of emission intensity versus time for the same size analyte for a prior conventional large volume spray chamber and an intra-microspray ICP torch of this invention.
Figure 5:
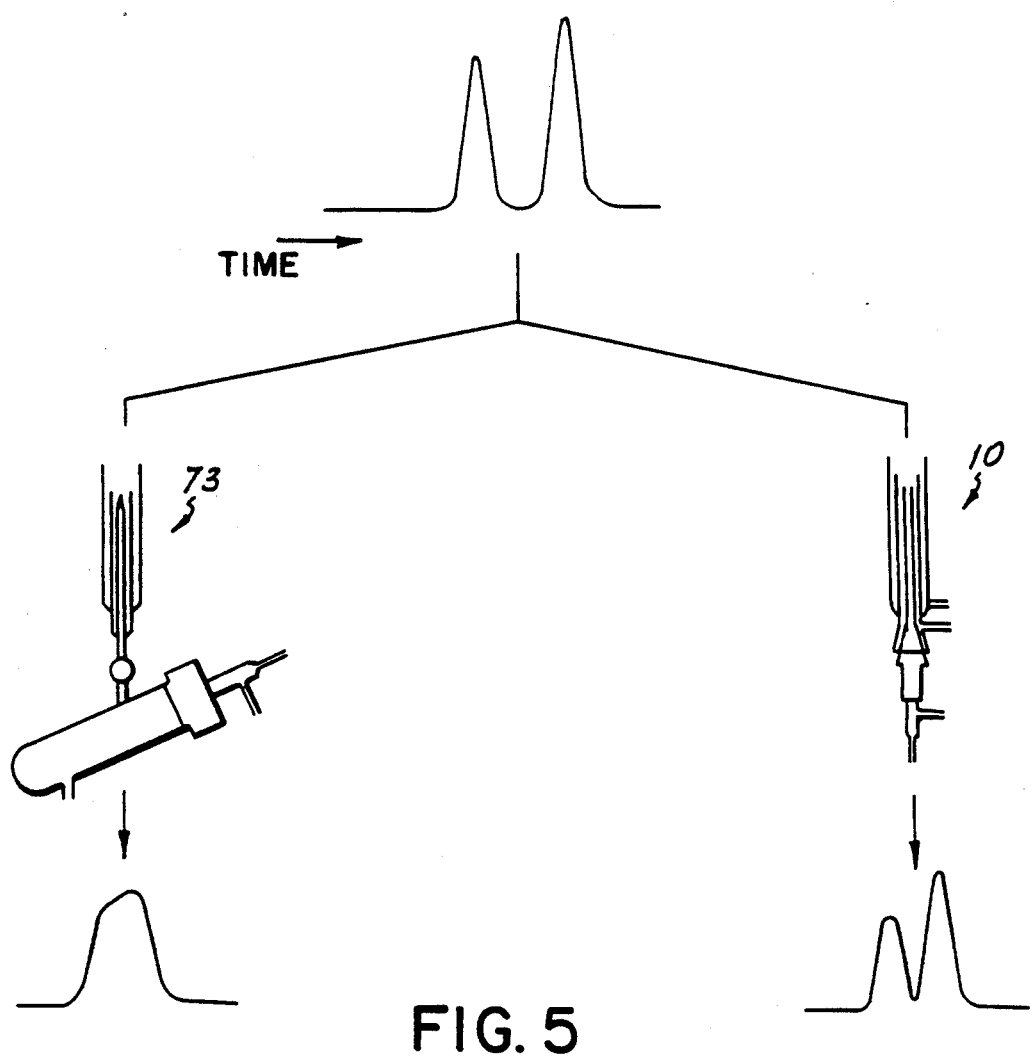
FIG. 5 illustrates a comparison of emission intensity versus time for a fluid containing two compounds for a prior conventional large volume spray chamber and an intra-microspray ICP torch of this invention.

In accordance with a preferred embodiment of the invention, as shown in FIGS. 2 and 3, each set of fingers includes three conically shaped fingers 48 that are integrally formed with the tube 27. The fingers 48 are preferably spaced equidistant around the inner circumference of the tube 27, centered at angles of about every 120° with respect to the center of the tube 27, as shown in FIG. 3. So as not to completely block the fluid path between adjacent chambers, the fingers 48 must be staggered somewhat along the length of the tube 27, so that there appears to be some overlap seen when looking down the length of the tube 27, which again is shown most clearly in FIG. 3. Each finger 48 has a radially extending, rounded tip 49, and each finger also tilts or recedes at a relatively low angle of inclination toward the plasma region 24. The tube 27 is preferably made of quartz, and the fingers 48 shaped by deforming the glass under high temperature.

Preferably, as shown in FIG. 1, a bottom end 50 of the intermediate tube 18 is outwardly flared to removably receive a correspondingly flared portion 51 of preshaped tube 27. The nebulizer 28 is then removably mounted within bottom end 30 of the tube 27 and held in place by O-rings 52. This construction enables the nebulizer 28 and the tube 27 to be easily assembled and disassembled from the rest of the torch 10 for cleaning or changing to a new test sample.

This construction also enables the tube 27 to be used in conjunction with an ICP torch of the type disclosed in applicant's U.S. Pat. No. 4,739,147. Accordingly, the tube 27 is preferably about 110 mm long. With the nebulizer 28 mounted, the distance between an exit nozzle 54 of the nebulizer 28 and an exit nozzle 56 of tube 27 is preferably about 85 mm. In FIG. 1, this distance is designated by numeral 57. The distance between exit nozzle 56 and the plasma region 24 is about 5 mm. The distance between nebulizer nozzle 54 and the first set 43 of fingers, designated generally by numeral 58, is about 25 mm, and the distance between the first and second sets of impaction means, 43 and 44, respectively, is preferably about 17 mm. For these dimensions, the final distance between the second set 44 of impactors and nozzle 56 is about 38 mm.

The preshaped tube 27 has an upper tapered portion 60, a lower tapered portion 61, and a middle portion 62 therebetween. At the midportion 62, the tube 27 has an outer diameter of about 8 mm and an inner diameter of about 6 mm. The fingers 48 extend radially about 4 mm across the inner diameter, and about 3 to 4 mm along the length of the tube 27. Upper tapered portion 60 is about 15 mm in length, converging to nozzle 56, which has an inner diameter of about 1 mm. Lower tapered portion 61 is also about 15 mm in length, the tube 27 diverging from the midportion 62 diameter to a maximum outer diameter of about 20 mm. A tube 27 having the above specified dimensions was manufactured by The Precision Glassblowing Co. of Colorado, and has proved suitable.

When connected to a pressurized fluid source through inlet 65 and a pressurized aerosol gas through inlet 66, the nebulizer 28 creates a pressurized mixture that is propelled from the nozzle 54 toward the lower set 43 of impaction fingers. Depending upon the sample to be tested, the gas pressure and the sample flow rate may vary. The flow of sample into the nebulizer 28 is preferably in the range of about 0.4 ml per min to 1 ml per min. With the aerosol gas connected at 56 pressurized in the range from about 60 to 90 psi, the pressurized mixture exits nozzle 54 at a rate of about 0.1 to 0.5 liters per minute. These operating conditions are reasonably close to those of the prior large volume systems, and a conventional peristaltic pump can be used to supply the desired fluid flow at the specified nebulizer back pressure range.

Upon contact with the inside walls of the tube 27 or the fingers 48, the larger size particles tend to either break up into smaller particles, or to condense and return under the force of gravity into the lower chamber for eventual collection through waste duct 68. Some of the larger particles will simply be too heavy to reach the first set of impaction fingers 43. These particles will fall under the force of their own weight, contacting the walls of the lower chamber 38 and eventually exiting through duct 68. Preferably, duct 68 has an outer diameter of about 3 mm and an inner diameter of about 2 mm, and the duct 68 is connected to one end of the peristaltic pump (not shown) so that condensed sample fluid is alternately aspirated out of the tube 27 between the pump strokes that supply sample fluid to the nebulizer 28.

The smaller size particles will be swept around the lower set of fingers 43, into the middle chamber 39, and toward the upper set of impaction fingers 44. Again, upon impact with the upper fingers 44, the relatively larger particles will either break up into smaller particles and pass into third chamber 40, or they will condense and eventually exit through duct 68. After passing into third chamber 40, the particles that are light enough to continue upward will exit through a nozzle 60 and into the plasma region 24. The pressure of the nebulizer 28 is, sufficient to maintain the upward movement of the sample toward the plasma region 24.

This structure promotes a steady flow of smaller, drier particles into the plasma region 24, while preventing the introduction into the plasma region 24 of the larger, wetter particles. Experimental evidence supports the claim that, with this invention, particles entering the plasma region 24 are about 15 microns. To confirm this, a method using a laser and sophisticated electronics developed on site was used to directly measure the size of aerosol particles exiting the tube 27. Commercially available as Laser Doppler Anemometry (LDA), the somewhat modified technique determines the size of a light-scattering object directly by interrogating two independent scattering signals for differences in phase. These two independent signals are measured at close to the same angle from the origination of the optical scattering except that the detectors are slightly displaced in space, whereby one detector is closer to the scattering origin than is the second. This slight separation in space yields a difference in the electronic signal from each detector that contains information related to the size of the original scattering object. The claimed invention was subjected to analysis by the above explained technique, with the result that particles no larger than 15 microns with a distribution of about an average of 6 microns exited the tube 27.

Compared to the prior large volume systems, the ICP torch 10 of this invention increases sample efficiency from about b 1-3% to about 4-5%. Historically, further increases in sample use efficiency without a corresponding removal of excess solvent from the aerosol has proved to be detrimental to analytical performances. This invention also reduces the amount of time required to change over to a new sample. Additionally, the ICP torch 10 of this invention provides a high degree of particle discrimination and speed retardation that simply cannot be obtained with a direct injection nebulizer. As a result, optimum clarity during spectrographic analysis is obtained.

FIG. 4 illustrates the advantages in high resolution chromatography provided by this invention over prior large volume systems. FIG. 4 shows two profiles of actual experimental data of intensity versus time for emission signals generated by the prior system and the ICP torch of this invention. The lower picture illustrates an analyte of a certain volume traversing along a solvent stream. This stream is water, but can be any suitable liquid of acceptable behavior. The analyte contains the element calcium, but can contain other elements typically determined by this technique.

When this water stream containing the analyte calcium is presented to both systems, two different emission profiles result. Note that, in the graph of intensity versus time, the trace for the prior large volume system, designated 70, takes more time to reach an equilibrium upper signal level than the trace recorded for the claimed invention, designated 71. This is due to the fact that the prior system requires a slower speed in order to accomplish sufficient nebulization. This slower speed also causes the signal for the large volume system to take longer to return to a baseline than the signal for the ICP torch of this invention. These profiles show that the claimed invention provides more rapid sample analysis and is less likely to cause cross-contamination of successive samples than the prior large volume system.

FIG. 5 illustrates this principle further in an application where a liquid chromatograph is interfaced to this invention, as for instance in size exclusion chromatography. For the prior large volume system, designated 73, as two successive eluting compounds come off the chromatography column, the probability is great that the successive eluting compounds will not be distinguishable in a plot of intensity versus time. On the other hand, with this invention 10, the two compounds will be resolved into separate peaks.

The ICP torch 10 of the invention is particularly advantageous with organic samples, which generally are heavier and require increased pressure in order to remain suspended. Typically, for prior systems, an increase in pressure decreased the sample travel time in the torch, which resulted in the formation of excessive vapor in the plasma region because the larger particles did not remain suspended long enough to be affected by gravity. However, compared to prior large volume systems, this invention enables pressure to be increased without causing excessive vapor formation. This is due to the presence of the impaction fingers, which inhibit vapor formation. The particles must move around the impactors, and, in doing so, they contact the walls of the tube, or the sides of the impactors, and/or the effects of gravity work upon the particles to break them down in size.

In addition to simplified assembly and disassembly, this structure provides an overall configuration that is more durable than the direct injection nebulizer and less bulky than the prior large volume spray chamber configuration.

While a preferred embodiment of the intramicrospray ICP torch has been described, it is to be understood that the invention is not limited thereby and that in light of the present disclosure, various other alternative embodiments will be apparent to one of ordinary skill in the art. Accordingly, it is to be understood that various changes may be made without departing from the scope of the invention as particularly set forth in the claims.

I claim:

1. An ICP torch comprising:
means for generating a high temperature ionized gas in a plasma region at one end of the torch;
multichamber particle discrimination means having first and second ends, the first end extending through said torch and terminating adjacent said plasma region;
a nebulizer mounted to said second end and adapted to propel a pressurized mixture of aerosol and sample particles through said multichamber particle discrimination means toward said plasma region;
impaction means positioned within said multichamber particle discrimination means and located within said torch, said impaction means adapted to divert flow of said pressurized mixture while enroute to said plasma region, thereby to produce a filtering effect to promote introduction into said plasma region of sample particles in the form of a fine mist wherein said multichamber particle discrimination means further comprises;
a preshaped tube concentrically mounted within said torch; and
said impaction means being directed radially inward to define adjacent chambers of said tube and to block a line of sight between said chambers.

2. The ICP torch of claim 1 wherein said impaction means are integrally formed with said tube.

3. The ICP torch of claim 1 wherein said multichamber particle discrimination means is detachably mounted to said torch.

4. The ICP torch of claim 3 wherein said nebulizer is removably mounted to said second end of said multichamber particle discrimination means.

5. The ICP torch of claim 1 wherein said multichamber particle discrimination means has a volume of about 2.5 milliliters.

6. An ICP torch comprising:
means for generating a high temperature ionized gas in a plasma region at one end of the torch;
multichamber particle discrimination means having first and second ends, the first end extending through said torch and terminating adjacent said plasma region;
a nebulizer mounted to said second end and adapted to propel a pressurized mixture of aerosol and sample particles through said multichamber particle discrimination means toward said plasma region; and
two spaced sets of impaction fingers positioned within aid multichamber particle discrimination means and defining three chambers located within said torch, each said set blocking the line of sight between two of said chambers, said impaction fingers adapted to divert flow of said pressurized mixture while enroute to said plasma region, thereby to produce a filtering effect to promote introduction into said plasma region of sample particles in the form of a fine mist.

7. The ICP torch of claim 6 wherein said set further comprises three fingers directed radially inward.

8. The ICP torch of claim 7 wherein the three impaction fingers of each said set are spaced equidistant around the inner circumference of said tube.

9. The ICP torch of claim 8 wherein the three impaction fingers of each said set are offset along the length of said tube.

10. The ICP torch of claim 6 wherein said impaction fingers are generally conical in shape, each said finger having an inwardly directed, rounded tip.

11. The ICP torch of claim 10 wherein said generally conically shaped impaction fingers tilt in the direction of said plasma region.

12. An ICP torch comprising:
means for generating a high temperature ionized gas in a plasma region at one end of the torch;
a multichamber particle discrimination means extending through said torch and terminating adjacent said plasma region for the passage of sample particles therethrough for introduction into said plasma region, said multichamber particle discrimination means including two spaced sets of inwardly directed impactors defining three chambers, each set of impactors blocking the line of sight between two adjacent chambers; and
a nebulizer mounted to said particle discrimination means for direct communication with a first of said chambers, said nebulizer adapted to propel a pressurized mixture of aerosol and said sample particles at a first of said sets of impactors and toward said plasma region, thereby to produce a filtering effect as said sample particles move toward said plasma region, said filtering effect promoting the passage of only sample particles having a size of about 15 microns or less.

13. An ICP torch comprising:
means for generating a high temperature ionized gas in a plasma region at one end of the torch;
a multichamber particle discrimination means extending through said torch and terminating adjacent said plasma region for the passage of sample particles therethrough for introduction into said plasma region, said multichamber particle discrimination means including two spaced sets of inwardly directed impactors defining three chambers, each set of impactors comprising three fingers integrally formed with said multichamber particle discrimination means and blocking the line of sight between two adjacent chambers; and
a nebulizer mounted to said particle discrimination means for direct communication with a first of said chambers, said nebulizer adapted to propel a pressurized mixture of aerosol and said sample particles at a first of said sets of impactors and toward said plasma region, thereby to produce a filtering effect as said sample particles move toward said plasma region, said filtering effect promoting the passage of only sample particles having a size of about 15 microns or less 14. An ICP torch comprising:
means for generating a high temperature ionized gas in a plasma region at one end of the torch;
a multichamber particle discrimination means extending through said torch and terminating adjacent said plasma region for the passage of sample particles therethrough for introduction into said plasma region, said multichamber particle discrimination means including two spaced sets of inwardly directed impactors defining three chambers, each set of impactors blocking the line of sight between two adjacent chambers;
a nebulizer mounted to said particle discrimination means for direct communication with a first of said chambers, said nebulizer adapted to propel a pressurized mixture of aerosol and said sample particles at a first of said sets of impactors and toward said plasma region, thereby to produce a filtering effect as said sample particles move toward said plasma region, said filtering effect promoting the passage of only sample particles having a size of about 15 microns or less; and venting means in communication with said first chamber for removing sample particles not introduced into said plasma region.

15. An ICP torch for generating a high temperature ionized gas in a plasma region at one end thereof, comprising:
a multichamber particle discrimination means adapted to project through said torch with a first end terminating adjacent said plasma region, said means adapted for passage therethrough of a sample to be introduced into said plasma region;
at least one set of radially inward directed impaction fingers integrally formed with said multichamber particle discrimination means, said fingers defining at least two adjacent chambers and blocking the line of sight between said chambers; and
a second end of said multichamber particle discrimination means adapted for removable receipt of a nebulizer aimed at said impaction fingers.

16. An ICP torch comprising:
a preshaped tube for conveying a fluid sample from a first end thereof to a second end thereof; and
at least one set of radially directed impactors extending into said tube, said set of impactors comprising three fingers spaced equidistant around the inner circumference of said tube and defining at least two chambers in said tube and each said set blocking the line of sight between two adjacent of said chambers.

17. The ICP torch of claim 16 wherein said fingers are offset along the length of said tube.

18. The ICP torch of claim 16 wherein said fingers are generally conical in shape, each said finger having an inwardly directed, rounded tip.

19. The ICP torch of claim 18 wherein said fingers tilt in the direction of said second end.

20. The ICP torch of claim 16 and further comprising:
two spaced sets of impactors defining three chambers within said tube, each set of impactors blocking the line of sight between two adjacent chambers.

21. The ICP torch of claim 20 wherein said second end of said tube converges to form an exit nozzle for said fluid sample, said first end of said tube is adapted for removable receipt of a nebulizer, and a flared midportion of said tube is adopted to circumferentially engage a similarly flared end of a torch conduit.

22. The ICP torch of claim 21 wherein said tube has walls that define a waste duct adjacent said first end.

* * * * *